United States Patent [19]

Yasui et al.

[11] Patent Number: 4,668,411
[45] Date of Patent: May 26, 1987

[54] DIUREA TYPE GREASE COMPOSITION

[75] Inventors: Hiroyoshi Yasui, Nara; Teruo Yoshida, Kashihara; Hiroshi Komiya, Nara; Toshitaro Oguchi, Nishinomiya; Seiji Okamura, Kobe, all of Japan

[73] Assignees: Koyo Seiko Co., Ltd.; Nippon Grease Co., Ltd., both of Osaka, Japan

[21] Appl. No.: 812,738

[22] Filed: Dec. 23, 1985

[30] Foreign Application Priority Data

Dec. 27, 1984 [JP] Japan ................................. 59-279734

[51] Int. Cl.$^4$ ........................................... C10M 115/04
[52] U.S. Cl. ............................................... 252/51.5 A
[58] Field of Search .................................... 252/51.5 A

[56] References Cited

U.S. PATENT DOCUMENTS

| 3,242,210 | 3/1966 | Dreher et al. | 252/51.5 A |
| 3,243,372 | 3/1966 | Dreher et al. | 252/51.5 A |
| 3,870,642 | 3/1975 | Gegner | 252/51.5 A |
| 3,920,571 | 11/1975 | Crucker | 252/51.5 A |
| 4,065,395 | 12/1977 | Bailey | 252/51.5 A |
| 4,115,284 | 9/1978 | Kinoshita et al. | 252/51.5 A |
| 4,261,844 | 4/1981 | Caruso | 252/51.5 A |
| 4,261,845 | 4/1981 | Cuscurida | 252/51.5 A |
| 4,263,156 | 4/1981 | Caruso | 252/51.5 A |
| 4,529,530 | 7/1985 | Shimizu et al. | 252/51.5 A |

*Primary Examiner*—Mark L. Bell
*Assistant Examiner*—Cynthia A. Prezlock
*Attorney, Agent, or Firm*—Larson and Taylor

[57] ABSTRACT

The present invention provides a grease composition comprising a lubricating oil and a thickener, characterized in that the thickener is a diurea compound prepared by reacting a diisocyanate compound with cyclohexylamine and monoalkylphenylamine wherein the alkyl portion has 8 to 16 carbon atoms.

10 Claims, No Drawings

DIUREA TYPE GREASE COMPOSITION

This invention relates to a novel diurea type grease composition.

As machines and devices are made more small-sized and lightweight in recent years, bearings, etc. for use therein are made greatly reduced in size and improved in performance. It is therefore required that lubricating greases for use in various bearings and the like exhibit higher performance at high temperatures and high speeds, have low torque properties and be usable stably for a prolonged period of time.

Lithium soap grease which is most widely used at present is usable under the conditions of up to 400,000 in dmn value [½ (bearing inside diameter (mm)+bearing outside diameter (mm)) x number of revolutions (r.p.m.)] and up to 120° C. in temperature but has the drawback that under conditions exceeding these limits, the grease softens, leaks markedly from the bearing and becomes unusable. Accordingly, thickeners have been developed as substitutes fr lithium soap. They include inorganic thickeners such as "Bentone 34" (brand name, product of NL Chemicals, U.S.A.) and "Aerosil" (brand name, product of Nippon Aerosil Co., Ltd., Japan), and organic thickeners such as copper phthalocyanine, sodium terephthalamate, diurea compounds and polyurea compounds.

Of these, the inorganic thickeners and organic thickeners containing metal have the drawback of deteriorating the lubricating oil by oxidation, so that the grease incorporating such thickener is not usable for a long period of time under high-temperature high-speed conditions. For example, greases containing the polyurea compound disclosed in U.S. Pat. No. 3,243,372 have the drawback of being thermally unstable and curing at high temperatures and are undesirable to use under the conditions of beyond 400,000 in dmn value and above 120° C. in temperature. Although greases are also developed with use of diurea compounds such as those disclosed in U.S. Pat. No. 2,710,841, these greases are still unsatisfactory in performance under high-temperature high-speed conditions.

Diurea compounds are prepared by reacting an amine with a diisocyanate compound and can be represented by the formula

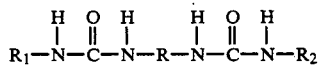

wherein R is the residue of the diisocyanate compound, and $R_1$ and $R_2$ are the same or different and are each an amine residue. While the characteristics of the grease prepared with use of the diurea compound differ greatly depending on the chemical structure of $R_1$ and $R_2$, the known diurea type greases have various drawbacks. For example, when $R_1$ and $R_2$ are each alkyl having at least 12 carbon atoms, the grease markedly softens and is therefore unusable at high temperatures. When $R_1$ and $R_2$ are each alkyl having up to 11 carbon atoms, the grease is fibrous, is liable to scatter under high-speed conditions and therefore has a shortened life. Further if $R_1$ and $R_2$ are each a compound having either an aromatic or alicyclic ring, the grease has poor mechanical stability under high-temperature conditions, leaks markedly from the bearing and accordingly has a shortened life. When the diurea compound disclosed in Examined Japanese Patent Publication SHO 55-11156 is used in which one of $R_1$ and $R_2$ is an alicyclic group and the other is a straight-chain alkyl, the grease is insufficient in mechanical stability under high-temperature conditions and liable to leak from bearings and has a relatively short life.

An object of the present invention is to provide a grease composition which is outstanding in mechanical stability, thermal stability and adhesion to bearings and the like even under high-temperature high-speed conditions and which therefore exhibits excellent overall performance at high temperatures, high speeds and low torques.

Another object of the present invention is to provide a grease composition which is usable stably for bearings, etc. for a prolonged period of time even under the high-temperature high-speed conditions, for example, of at least 500,000 in dmn value and at least 130° C. in temperature.

These and other objects of the present invention will become apparent from the following description.

The present invention provides a grease composition comprising a lubricating oil and a thickener, characterized in that the thickener is a diurea compound prepared by reacting a diisocyanate compound with cyclohexylamine and monoalkylphenylamine wherein the alkyl portion has 8 to 16 carbon atoms.

The research conducted by the present inventors has revealed the following.

(1) When a diurea compound prepared by reacting a diisocyanate compound with cyclohexylamine and monoalkylphenylamine wherein the alkyl portion has 8 to 16 carbon atoms is used as a thickener for preparing a grease composition, the grease composition obtained exhibits outstanding properties in respect of mechanical stability, thermal stability and adhesion to bearings, etc. even under high-temperature high-speed conditions.

(2) The grease composition is therefore excellent in overall performance at high temperatures, high speeds and low torques.

(3) Accordingly the grease composition is usable stably for bearings and the like for a prolonged period of time even under the high-temperature high-speed conditions, for example, of at least 500,000 in dmn value and at least 130° C. in temperature.

The present invention has been accomplished based on these novel findings.

According to the present invention, it is essential to use as a thickener a diurea compound which is obtained by reacting a diisocyanate compound with cyclohexylamine and monoalkylphenylamine wherein the alkyl portion has 8 to 16 carbon atoms.

The alkyl portion having 8 to 16 carbon atoms of the monoalkylphenylamine may have a straight chain or be branched. This amine may be a mixture of an amine having a straight-chain alkyl portion and an amine having a branched alkyl portion. The alkyl portion may be substituted at any of the ortho-, meta- and para-positions. A mixture of such amines are usable which differ in the position of substitution of alkyl portion. Stated more specifically, examples of useful amines are octylaniline, decylaniline, dodecylaniline, tetradecylaniline, hexadecylaniline, isododecylaniline and the like. Of these examples, more preferred monoalkylphenylamines are those wherein the alkyl portion has 8 to 12 carbon atoms, such as octylaniline, decylaniline and dodecylaniline, and the most preferred is p-dodecylaniline. The contemplated effect of the invention is not obtainable with use of amines wherein the number of carbon atoms of the alkyl portion is not in the range of from 8 to 16.

Any of the diisocyanate compounds heretofore used is effectively usable as it is as the diisocyanate compound for the present invention. It is desirable to use aromatic diisocyanate compounds. Examples of such compounds are 4,4'-diphenylmethane diisocyanate, 2,4-tolylene diisocyanate, 2,6-tolylene diisocyanate, p-phenylene diisocyanate, 3,3'-dimethyl-4,4'-diphenylmethane diisocyanate and the like.

A molar ratio of the monoalkylphenylamine to cyclohexylamine to be used in this invention is usually about 1:9 to about 9:1, preferably about 3:7 to about 7:3. The amines are preferably used in mixture and the amine mixture is reacted with the diisocyanate compound usually in the ratio of about 2 moles of the former per mole of the latter, as is generally the case with reactions of this kind.

The lubricating oil to be used in this invention can be any of those conventionally used for greases, such as mineral olis of the paraffin type and naphthene type, synthetic oils of the ester type, hydrocarbon type and silicone type, and mixtures of such oils. Since the grease is used at a high temperature for a long period of time, it is desirable to use a synthetic oil which has good thermal stability, or a mixture of synthetic oil and mineral oil. While the viscosity of the lubricating oil may be in the usual range, the preferred viscosity is in the range of about 2 to about 20 cst at 100° C. in view of torque characteristics.

The grease composition of the present invention is prepared preferably by reacting the amine mixture with the diisocyanate compound in a lubricating oil to produce a diurea compound.

By reacting the amine mixture with the diisocyanate compound in the lubricating oil, a reaction product of high homegeneity can be obtained. The reaction may be conducted by adding a solution of diisocyanate compound in lubricating oil to a solution of amine mixture in lubricating oil, or conversely, by adding the latter solution to the former solution. Further alternatively, a solution of monoalkylphenylamine in lubricating oil may be added to a solution of diisocyanate compound in lubricating oil, and a solution of cyclohexylamine in lubricating oil added to the resulting mixture. The solutions may be added in an order reverse to the above. These three solutions may be prepared separately and then mixed together at the same time. The reaction temperature and time are not limited specifically. Thus, the reaction is conducted at about 40° to 150° C. for about 5 minutes to about 2 hours as is usually the case with reactions of this kind.

To disperse the resulting diurea compound in the lubricating oil completely, the reaction mixture is heated at about 130° to about 210° C., preferably about 140° to about 190° C., with stirring, then cooled to a temperature of up to 120° C., and thereafter thoroughly treated by a homogenizer, three-roll mill or the like, whereby a grease composition is obtained.

The diurea type grease composition of the present invention contains the diurea compound in an amount usually of about 0.3 to about 30 parts by weight, preferably about 7 to about 25 parts by weight, per 100 parts by weight of the lubricating oil, as is generally the case with conventional greases.

When required, additives such as antioxidant, rust inhibitor, extreme pressure agent and the like can be suitably added to the diurea grease composition of the present invention. Also effectively usable are additives such as alkenyl succinimide, metal salts of alkylbenzenesulfonic acids and metal salts of petroleum sulfonic acid which have been developed by the present applicant for giving improved air borne noise characteristics to diurea greases (Unexamined Japanese Patent Publication SHO 58-185693).

Thus, the diurea type grease composition of the present invention can be obtained which is usable stably for a prolonged period of time under high-temperature high-speed conditions.

The present invention will be described in greater detail with reference to the following examples and comparative examples.

EXAMPLE 1

| Paraffin type mineral oil | 1700 g |
| (11 cst in viscosity at 100° C.) | |
| 4,4'-Diphenylmethane diisocyanate | 122 g |
| p-Dodecylaniline | 128 g |
| Cyclohexylamine | 50 g |
| Antioxidant | 40 g |

4,4'-Diphenylmethane diisocyanate (122 g) was dissolved in 850 g of the above mineral oil with stirring and heating at 100° C. Separately, 128 g of p-dodecylaniline and 50 g of cyclohexylamine were dissolved in 850 g of the mineral oil with stirring and heating at 60° C. The amine mixture solution was slowly added to the diisocyanate solution with stirring. To uniformly disperse the resulting diurea compound in the mineral oil, the reaction mixture was heated to 150° C. with stirring, maintained at this temperature for 15 to 30 minutes and thereafter cooled to 100° C. with stirring. An antioxidant (40 g) was added to the mixture, and the resulting mixture was treated by three-roll mill to obtain a grease composition of the present invention.

EXAMPLE 2

| Paraffin type mineral oil | 1700 g |
| (11 cst in viscosity at 100° C.) | |
| 3,3'-Dimethyl-4,4'-Diphenylmethane diisocyanate | 131 g |
| p-Dodecylaniline | 123 g |
| Cyclohexylamine | 46 g |
| Antioxidant | 40 g |

A grease composition of the invention was prepared in the same manner as in Example 1 except that 3,3'-dimethyl-4,4'-diphenylmethane diisocyanate was used in place of 4,4'-diphenylmethane diisocyanate.

EXAMPLE 3

| Synthetic hydrocarbon oil | 1620 g |
| (poly-α-olefin type, | |
| 8 cst in viscosity at 100° C.) | |
| 4,4'-Diphenylmethane diisocyanate | 174 g |
| p-Dodecylaniline | 109 g |
| Cyclohexylamine | 97 g |
| Antioxidant | 40 g |

4,4'-Diphenylmethane diisocyanate (174 g) was dissolved in 810 g of the above synthetic hydrocarbon oil with stirring and heating at 100° C. Separately, 109 g of p-dodecylaniline and 97 g of cyclohexylamine were dissolved in 810 g of the oil with stirring and heating at 60° C. The amine mixture solution was slowly added to the diisocyanate solution with stirring. To uniformly disperse the resulting diurea compound in the synthetic hydrocarbon oil, the mixture was heated to 180° C. with stirring. The same procedure as in Example 1 was thereafter followed to obtained a grease composition of the invention.

EXAMPLE 4

| | |
|---|---|
| Pentaerythritol ester (6 cst in viscosity at 100° C.) | 1700 g |
| 4,4'-Diphenylmethane diisocyanate | 122 g |
| p-Dodecylaniline | 128 g |
| Cyclohexylamine | 50 g |
| Antioxidant | 40 g |

A grease composition of the present invention was prepared in the same manner as in Example 1 except that pentaerythritol ester was used in place of mineral oil.

EXAMPLE 5

| | |
|---|---|
| Synthetic hydrocarbon oil (poly-α-olefin type, 8 cst in viscosity at 100° C.) | 1700 g |
| 4,4'-Diphenylmethane diisocyanate | 122 g |
| p-Dodecylaniline | 128 g |
| Cyclohexylamine | 50 g |
| Petroleum calcium sulfonate | 30 g |
| Antioxidant | 40 g |

4,4'-Diphenylmethane diisocyanate (122 g) and 30 g of petroleum calcium sulfonate (additive for giving improved air borne noise characteristics) were dissolved in 850 g of the above oil with stirring and heating at 100° C. The same procedure as in Example 1 was thereafter followed to obtained a grease composition of the invention.

EXAMPLE 6

| | |
|---|---|
| Synthetic hydrocarbon oil (poly-α-olefin type, 8 cst in viscosity at 100° C.) | 1600 g |
| 4,4'-Diphenylmethane diisocyanate | 111 g |
| p-Dodecylaniline | 162 g |
| Cyclohexylamine | 27 g |
| Antioxidant | 40 g |

4,4' Diphenylmethane diisocyanate (111 g) was dissolved in 800 g of the above oil with stirring and heating at 100° C. Separately, 162 g of p-dodecylaniline and 27 g of cyclohexylamine were dissolved in 800 g of the oil with stirring and heating at 60° C. The same procedure as in Example 1 was thereafter followed to prepare a grease composition of the invention.

EXAMPLE 7

| | |
|---|---|
| Paraffin type mineral oil (11 cst in viscosity at 100° C.) | 1700 g |
| 4,4'-Diphenylmethane diisocyanate | 122 g |
| p-Dodecylaniline | 128 g |
| Cyclohexylamine | 50 g |
| Antioxidant | 40 g | p-Dodecylaniline (128 g) and 50 g of cyclohexylamine were dissolved in 850 g of the above mineral oil with stirring and heating at 60° C. Separately, 122 g of 4,4'-diphenylmethane diisocyanate was dissolved in 850 g of the oil with stirring and heating at 100° C. The diisocyanate solution was slowly added to the amine mixture solution with stirring to produce a diurea compound. The same procedure as in Example 1 was thereafter followed to obtain a grease composition of the invention.

EXAMPLE 8

| | |
|---|---|
| Paraffin type mineral oil (11 cst in viscosity at 100° C.) | 1700 g |
| 4,4'-Diphenylmethane diisocyanate | 122 g |
| p-Dodecylaniline | 128 g |
| Cyclohexylamine | 50 g |
| Antioxidant | 40 g |

4,4'-Diphenylmethane diisocyanate (122 g) was dissolved in 800 g of the above mineral oil with stirring and heating at 100° C. Separately, 128 g of p-dodecylaniline was dissolved in 600 g of the mineral oil with stirring and heating at 60° C. This solution was slowly added to the diisocyanate solution with stirring. After completion of the addition, a solution of 50 g of cyclohexylamine in 300 g of the mineral oil was added to the mixture to produce a diurea compound. The same procedure as in Example 1 was thereafter followed to obtain a grease composition of the invention.

EXAMPLE 9

| | |
|---|---|
| Paraffin type mineral oil (11 cst in viscosity at 100° C.) | 1640 g |
| 4,4'-Diphenylmethane diisocyanate | 163 g |
| Octylaniline | 133 g |
| Cyclohexylamine | 64 g |
| Antioxidant | 40 g |

A grease composition of the invention was prepared in the same manner as in Example 1 except that octylaniline was used in place of p-dodecylaniline.

COMPARATIVE EXAMPLE 1

| | |
|---|---|
| Paraffin type mineral oil (11 cst in viscosity at 100° C.) | 1700 g |
| 4,4'-Diphenylmethane diisocyanate | 97 g |
| p-Dodecylaniline | 203 g |
| Antioxidant | 40 g |

4,4'-Diphenylmethane diisocyanate (97 g) was dissolved in 850 g of the above oil with stirring and heating at 100° C. Separately, 203 g of p-dodecylaniline was dissolved in 850 of the oil with stirring and heating at 60° C. The same procedure as in Example 1 was thereafter followed to prepare a grease composition for comparison.

COMPARATIVE EXAMPLE 2

| | |
|---|---|
| Paraffin type mineral oil (11 cst in viscosity at 100° C.) | 1700 g |
| 4,4'-Diphenylmethane diisocyanate | 96 g |
| p-Dodecylaniline | 101 g |
| Stearylamine | 103 g |
| Antioxidant | 40 g |

A grease composition for comparison was prepared in the same manner as in Example 1 except that stearylamine was used in place of cyclohexylamine.

COMPARATIVE EXAMPLE 3

| | |
|---|---|
| Synthetic hydrocarbon oil (poly-α-olefin type, 8 cst in viscosity at 100° C.) | 1700 g |
| 4,4'-Diphenylmethane diisocyanate | 164 g |
| Toluidine | 71 g |
| Cyclohexylamine | 65 g |
| Antioxidant | 40 g |

A grease composition for comparison was prepared in the same manner as in Example 1 with the exception of using the above oil in place of the paraffin type mineral oil and using toluidine in place of p-dodecylaniline.

COMPARATIVE EXAMPLE 4

| | |
|---|---|
| Paraffin type mineral oil (11 cst in viscosity at 100° C.) | 1700 g |
| 4,4'-Diphenylmethane diisocyanate | 125 g |
| p-Dodecylaniline | 131 g |
| 1,2-Dimethylpropylamine | 44 g |
| Antioxidant | 40 g |

A grease composition for comparison was prepared in the same manner as in Example 1 except that cyclohexylamine was replaced by 1,2-dimethylpropylamine.

COMPARATIVE EXAMPLE 5

| | |
|---|---|
| Paraffin type mineral oil (11 cst in viscosity at 100° C.) | 1700 g |
| 4,4'-Diphenylmethane diisocyanate | 115 g |
| Stearylamine | 123 g |
| Isopropylamine | 62 g |
| Antioxidant | 40 g |

4,4'-Diphenylmethane diisocyanate (115 g) was dissolved in 850 g of the above oil with stirring and heating at 100° C. Separately, 123 g of stearylamine and 62 g of isopropylamine were dissolved in 850 of the oil with stirring and heating at 60° C. The same procedure as in Example 1 was thereafter followed to prepare a grease composition for comparison.

COMPARATIVE EXAMPLE 6

| | |
|---|---|
| Paraffin type mineral oil (11 cst in viscosity at 100° C.) | 1700 g |
| 4,4'-Diphenylmethane diisocyanate | 168 g |
| Cyclohexylamine | 132 g |
| Antioxidant | 40 g |

4,4'-Diphenylmethane diisocyanate (168 g) was dissolved in 850 g of the above oil with stirring and heating at 100° C. Separately, 132 g of cyclohexylamine was dissolved in 850 of the oil with stirring and heating at 60° C. The same procedure as in Example 1 was thereafter followed to obtain a grease composition for comparison.

COMPARATIVE EXAMPLE 7

| | |
|---|---|
| Paraffin type mineral oil (11 cst in viscosity at 100° C.) | 1760 g |
| 4,4'-Diphenylmethane diisocyanate | 97 g |
| Cyclohexylamine | 38 g |
| Stearylamine | 105 g |
| Antioxidant | 40 g |

4,4'-Diphenylmethane diisocyanate (97 g) was dissolved in 880 g of the above oil with stirring and heating at 100° C. Separately, 38 g of cyclohexylamine and 105 g of stearylamine were dissolved in 880 of the oil with stirring and heating at 60° C. The same procedure as in Example 1 was thereafter followed to obtain a grease composition for comparison.

The grease compositions prepared in Examples 1 to 9 and Comparative Examples 1 to 7 were tested for performance by the following methods.

Worked Penetration

The specimen was measured for consistency immediately after 60 strokes using a grease worker prescribed in JIS K 2220 (Grease) 5.3.

Roll Stability

The specimen was tested at 130° C. for 24 hours using a tester prescribed in ASTM D 1831 and thereafter measured at 25° C. for worked penetration by the ½ scale penetration test method according to JIS K 2220, Reference 1. The difference in worked penetration before and after the test is shown. The symbol + indicates softening.

Leakage of Grease

The specimen (1.60 g) was filled in a sealed type deep groove ball bearing 6204ZZ, which was then operated at 15000 r.p.m. (500,000 in dmn value) at an air bath temperature of 130° C. for 20 hours to determine the amount of specimen leaking from the interior of the bearing. The ratio (%) of the amount of leak relative to the amount initially enclosed in the bearing is shown.

Grease Life

The same bearing as used for the determination of leakage was operated under the same conditions with the specimen enclosed therein. The result is given in terms of the total period of time (hours) when the torque value reached 5000 g-mm.

Table 1 shows the test results.

TABLE 1

| | Test item | | | |
|---|---|---|---|---|
| Composition | Worked penetration | Roll stability | Leakage (%) | Grease life (hr.) |
| Example | | | | |
| 1 | 252 | +20 | 3.2 | 2200 |
| 2 | 248 | +70 | 5.6 | 1800 |
| 3 | 217 | +56 | 5.1 | 2700 |
| 4 | 255 | +75 | 3.5 | 2850 |
| 5 | 251 | +45 | 3.0 | 2500 |
| 6 | 242 | +50 | 2.8 | 2600 |
| 7 | 250 | +22 | 4.3 | 2300 |
| 8 | 261 | +25 | 5.3 | 2350 |
| 9 | 267 | +30 | 5.8 | 1900 |
| Comp. Example | | | | |
| 1 | 290 | At least +160 | 13.1 | 500 |
| 2 | 222 | +118 | 8.0 | 700 |
| 3 | 260 | +149 | 7.8 | 1050 |
| 4 | 213 | +109 | 13.1 | 850 |
| 5 | 200 | +170 | 15.0 | 450 |
| 6 | 272 | At least +160 | 15.0 | 700 |

TABLE 1-continued

| | Test item | | | |
|---|---|---|---|---|
| Composition | Worked penetration | Roll stability | Leakage (%) | Grease life (hr.) |
| 7 | 195 | +130 | 8.2 | 1250 |

Table 1 shows that the grease compositions of Examples are exceedingly smaller in the variation in the roll stability and thus higher in mechanical stability than those of Comparative Examples.

The grease compositions of Examples are outstanding in thermal stability, mechanical stability, adhesion to bearings, etc. and are therefore much less susceptible to leakage than those of Comparative Examples. This indicates that the compositions of Examples, which are highly stable thermally and mechanically, suitably channel within bearings without being agitated excessively and satisfactorily remain in the bearing. On the other hand, the compositions of Comparative Examples soften when heated, become churned, i.e., excessively agitated within the bearing owing to low mechanical stability, markedly leak on softening and fail to remain within the bearing because of poor adhesion.

The life values determined indicate that the grease compositions of Examples are excellent in overall performance at high temperatures, high speeds and low torques and are serviceable for at least 1.5 to 2 times longer period than those of Comparative Examples.

The above results indicate that the grease compositions of the present invention are usable stably over a prolonged period of time even under the high-temperature high-speed conditions, for example, of at least 500,000 in dmn value and at least 130° C. in temperature.

We claim:

1. A grease composition comprising a lubricating oil and a thickener, characterized in that the thickener is a diurea compound prepared by reacting a diisocyanate compound with cyclohexylamine and monoalkylphenylamine wherein the alkyl portion has 8 to 16 carbon atoms.

2. A grease composition as defined in claim 1 wherein the monoalkylphenylamine is at least one of octylaniline, decylaniline, dodecylaniline, tetradecylaniline, hexadecylaniline and isododecylaniline.

3. A grease composition as defined in claim 1 wherein the alkyl portion of the monoalkylphenylamine has 8 to 12 carbon atoms.

4. A grease composition as defined in claim 3 wherein the monoalkylphenylamine is at least one of octylaniline, decylaniline and dodecylaniline.

5. A grease composition as defined in claim 4 wherein the monoalkylphenylamine is p-dodecylaniline.

6. A grease composition as defined in claim 1 wherein the diisocyanate compound is an aromatic diisocyanate compound.

7. A grease composition as defined in claim 1 wherein a molar ratio of monoalkylphenylamine to cyclohexylamine is about 1:9 to about 9:1.

8. A grease composition as defined in claim 7 wherein the monoalkylphenylamine to cyclohexylamine molar ratio is about 3:7 to about 7:3.

9. A grease composition as defined in claim 1 wherein the amines are reacted with the diisocyanate compound in the lubricating oil.

10. A grease composition as defined in claim 1 which comprises about 0.3 to about 30 parts by weight of the diurea compound per 100 parts by weight of the lubricating oil.

* * * * *